US012799078B2

(12) United States Patent
Basset et al.

(10) Patent No.: US 12,799,078 B2
(45) Date of Patent: Nov. 17, 2026

(54) PROCESS FOR MAKING A TASTE-MODIFYING COMPOUND

(71) Applicant: Firmenich SA, Satigny (CH)

(72) Inventors: Jean-Francois Basset, Satigny (CH); Eric Walther, Satigny (CH); Herve Mosimann, Satigny (CH); Harvey Randall, Satigny (CH); Simon Linder, Satigny (CH); Maurus Marty, Satigny (CH)

(73) Assignee: Firmenich SA, Satigny (CH)

( * ) Notice: Subject to any disclaimer, the term of this patent is extended or adjusted under 35 U.S.C. 154(b) by 247 days.

(21) Appl. No.: 18/850,714

(22) PCT Filed: Apr. 28, 2023

(86) PCT No.: PCT/EP2023/061221
§ 371 (c)(1),
(2) Date: Sep. 25, 2024

(87) PCT Pub. No.: WO2023/209143
PCT Pub. Date: Nov. 2, 2023

(65) Prior Publication Data

US 2025/0223261 A1 Jul. 10, 2025

Related U.S. Application Data

(60) Provisional application No. 63/336,360, filed on Apr. 29, 2022.

(30) Foreign Application Priority Data

May 5, 2022 (EP) .................................... 22171711

(51) Int. Cl.

| | |
|---|---|
| ***C07D 215/54*** | (2006.01) |
| ***A23L 27/00*** | (2016.01) |
| ***A23L 27/20*** | (2016.01) |
| ***A23L 27/30*** | (2016.01) |
| ***C07C 253/30*** | (2006.01) |

(52) U.S. Cl.
CPC ........ *C07D 215/54* (2013.01); *A23L 27/2054* (2016.08); *A23L 27/30* (2016.08); *A23L 27/88* (2016.08); *C07C 253/30* (2013.01)

(58) Field of Classification Search
CPC .................................................... C07D 215/54
See application file for complete search history.

(56) References Cited

FOREIGN PATENT DOCUMENTS

WO WO 2013/025560 2/2013

OTHER PUBLICATIONS

Sestili, I. et al. Eur. J. Med. Chem. 2004, 39, 1047-1057 (Year: 2004).*
Doucet-Personeni, C. et al. J. Med. Chem. 2001, 44, 3203-3215 (Year: 2001).*
Veronese, A. C. et al. Tetrahedron 1995, 51, 12277-12284 (Year: 1995).*
Sivaraman et al., Synthesis of 4-methyl-2,3-disubstituted quinoline scaffolds via environmentally benign Fe(III) catalysed sequential condensation, cyclization and aromatization of 1,3-diketone and 2-ethynylaniline, RSC Advances, 4(94):52060-52066.
International search report and written opinion dated Nov. 2, 2023 in application No. PCT/EP2023/061221.

* cited by examiner

*Primary Examiner* — Andrew D Kosar
*Assistant Examiner* — Connor K English
(74) *Attorney, Agent, or Firm* — Knobbe, Martens, Olson & Bear, LLP

(57) ABSTRACT

The present disclosure generally relates to an improved process for making certain aminoquinoline compounds that have utility as sweeteners and sweetness-enhancing agents. In certain aspects, the disclosure provides a method of making certain such aminoquinoline compounds by a process that includes reacting an aminobenzonitrile compound with an alkyl acetoacetate compound to form an enaminonitrile compound that is subsequently converted to an aminoquinoline compound.

12 Claims, 2 Drawing Sheets

Hydroxypivalic acid

PROCESS FOR MAKING A TASTE-MODIFYING COMPOUND

TECHNICAL FIELD

The present disclosure generally relates to an improved process for making certain aminoquinoline compounds that have utility as sweeteners and sweetness-enhancing agents. In certain aspects, the disclosure provides a method of making certain such aminoquinoline compounds by a process that includes reacting an aminobenzonitrile compound with an alkyl acetoacetate compound to form an enaminonitrile compound that is subsequently converted to an aminoquinoline compound.

DESCRIPTION OF RELATED ART

Certain classes of aminoquinoline compounds have utility as sweeteners and sweetness enhancers. Non-limiting examples of such compounds are set forth in PCT Publication No. WO 2013/025560. In that publication, the compounds are synthesized in small quantities suitable for use in cellular screening assays and simple sensory testing. Thus, the synthetic methods described in the publication may not be suitable for the manufacture of industrial-scale quantities of these compounds.

Industrial-scale synthesis of fine chemicals often imposes restrictions on the process that are less relevant to laboratory-scale syntheses. For example, laboratory-scale synthesis may use certain compounds that pose a fire or explosion risks or compounds that may pose health or safety risks for humans. In the laboratory setting, such risks can be substantially mitigated by performing the syntheses in vented hoods, protective boxes, and the like. But such risk-mitigation strategies cannot be easily carried over into an industrial setting. Therefore, there is a continuing need to develop synthetic methods of making certain compounds that use reagents and conditions whose risks can be easily managed and mitigated when these compounds are made in industrially relevant quantities.

SUMMARY

The present disclosure provides methods of synthesizing certain aminoquinoline compounds using reagents and conditions that are suitable for industrial scale.

In at least one aspect, the disclosure provides methods of making a compound of formula (Ia)

(Ia)

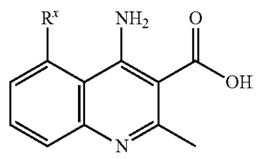

or a comestibly acceptable salt thereof, the method comprising:

(a) reacting a compound of formula (Ib)

(Ib)

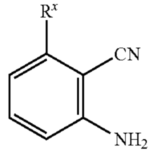

with a compound of formula (Ic)

(Ic)

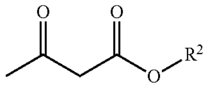

to form a compound of formula (Id)

(Id)

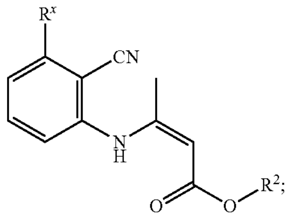

; and and (b) reacting the compound of formula (Id) of (a) to form a compound of formula (Ia); Wherein: $R^x$ is —F or —O—$R^1$; $R^1$ is $C_{1-20}$ hydrocarbyl, where one or more of the carbon atoms of the hydrocarbyl group are replaced by nitrogen, oxygen, or sulfur; and $R^2$ is $C_{1-6}$ alkyl.

Further aspects, and embodiments thereof, are set forth below in the Detailed Description, the Drawings, the Abstract, and the Claims.

BRIEF DESCRIPTION OF THE DRAWINGS

The drawings are provided for illustrative purposes only, and are not intended to describe any preferred compositions or preferred methods, or to serve as a source of any limitations on the scope of the claimed inventions.

DETAILED DESCRIPTION

Figure 1:
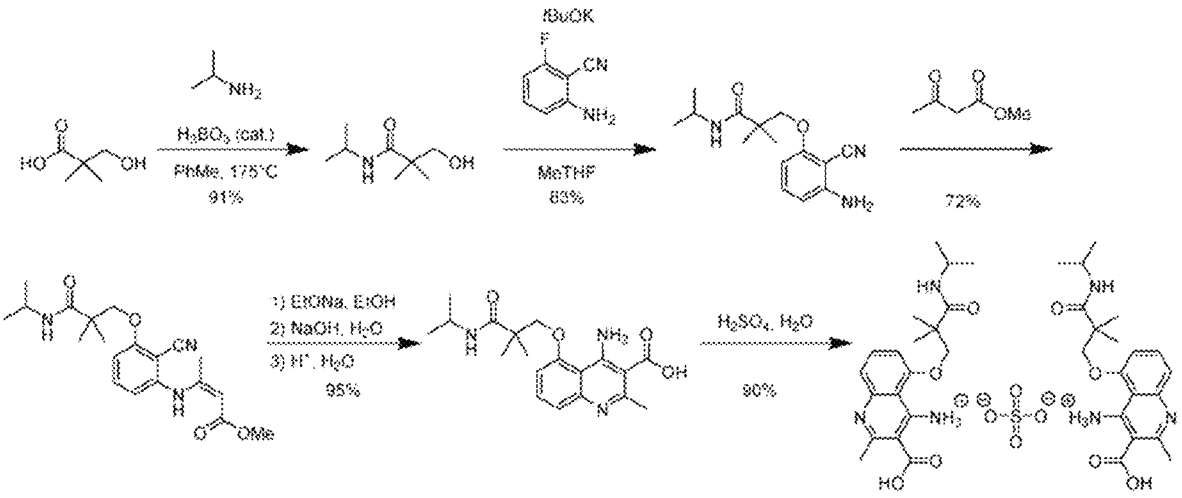
FIG. 1 shows a process scheme for making a sulfate salt of an aminoquinoline compound according to one embodiment of the methods set forth herein.
Figure 2:
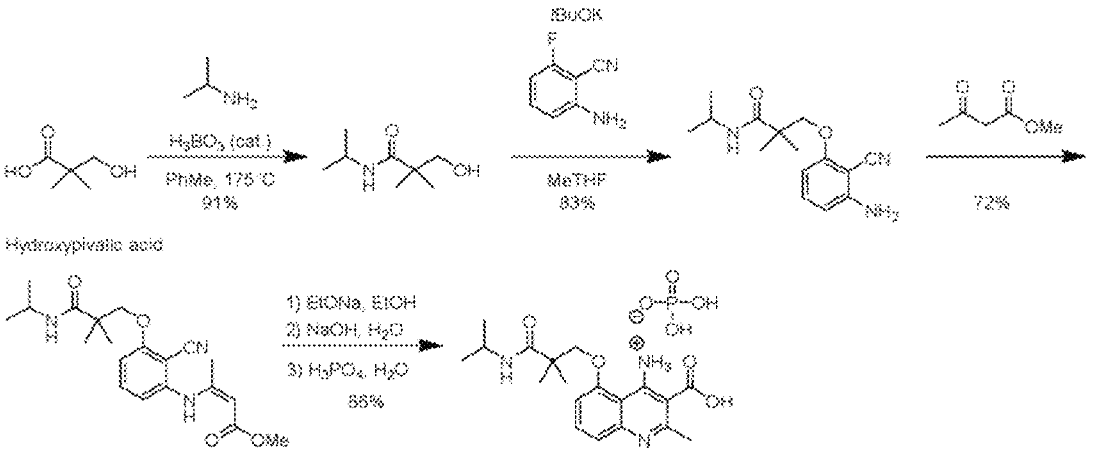
FIG. 2 shows a process scheme for making a phosphate salt of an aminoquinoline compound according to one embodiment of the methods set forth herein.

The following Detailed Description sets forth various aspects and embodiments provided herein. The description is to be read from the perspective of the person of ordinary skill in the relevant art. Therefore, information that is well known to such ordinarily skilled artisans is not necessarily included.

DEFINITIONS

The following terms and phrases have the meanings indicated below, unless otherwise provided herein. This disclosure may employ other terms and phrases not expressly defined herein. Such other terms and phrases have the meanings that they would possess within the context of this disclosure to those of ordinary skill in the art. In some instances, a term or phrase may be defined in the singular or plural. In such instances, it is understood that any term in the singular may include its plural counterpart and vice versa, unless expressly indicated to the contrary As used herein, the singular forms "a," "an," and "the" include plural referents unless the context clearly dictates otherwise. For example, reference to "a substituent" encompasses a single substituent as well as two or more substituents, and the like.

As used herein, "for example," "for instance," "such as," or "including" are meant to introduce examples that further clarify more general subject matter. Unless otherwise expressly indicated, such examples are provided only as an aid for understanding embodiments illustrated in the present disclosure, and are not meant to be limiting in any fashion. Nor do these phrases indicate any kind of preference for the disclosed embodiment.

As used herein, "comprise" or "comprises" or "comprising" or "comprised of" refer to groups that are open, meaning that the group can include additional members in addition to those expressly recited. For example, the phrase, "comprises A" means that A must be present, but that other members can be present too. The terms "include," "have," and "composed of" and their grammatical variants have the same meaning. In contrast, "consist of" or "consists of" or "consisting of" refer to groups that are closed. For example, the phrase "consists of A" means that A and only A is present.

As used herein, "optionally" means that the subsequently described event(s) may or may not occur. In some embodiments, the optional event does not occur. In some other embodiments, the optional event does occur one or more times.

As used herein, "or" is to be given its broadest reasonable interpretation, and is not to be limited to an either/or construction. Thus, the phrase "comprising A or B" means that A can be present and not B, or that B is present and not A, or that A and B are both present. Further, if A, for example, defines a class that can have multiple members, e.g., $A_1$ and $A_2$, then one or more members of the class can be present concurrently.

As used herein, "hydrocarbyl" refers to a functional group consisting of carbon and hydrogen atoms. Such groups can be aliphatic, aromatic, or a mixture of aliphatic or aromatic groups. In some cases and where indicated, one or more carbon atoms of the hydrocarbyl moiety may be optionally replaced by a heteroatom (such as nitrogen, oxygen, or sulfur). Even when such replacements occur, the moiety will continue to have at least one carbon atom.

As used herein, "alkyl" means a straight or branched hydrocarbon chain that is fully saturated (i.e., contains no double or triple bonds). In some embodiments, an alkyl group has 1 to 20 carbon atoms (whenever it appears herein, a numerical range such as "1 to 20" refers to each integer in the given range; for example, "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 9 carbon atoms. The alkyl group could also be a lower alkyl having 1 to 4 carbon atoms. The alkyl group may be designated as "$C_{1-4}$ alkyl" or similar designations. By way of example only, "$C_{1-4}$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertbutyl, pentyl, hexyl, and the like. Unless indicated to the contrary, the term "alkyl" refers to a group that is not further substituted.

As used herein, "heteroalkyl" means a straight or branched hydrocarbon chain containing one or more heteroatoms, that is, an element other than carbon, including but not limited to, nitrogen, oxygen, and sulfur. In some cases, the "heteroalkyl" groups contain unsaturation, such as when the "heteroalkyl" group contains an oxo moiety. In some embodiments, the heteroalkyl group has from 1 to 20 carbon atom, although the present definition also covers the occurrence of the term "heteroalkyl" where no numerical range is designated. The heteroalkyl group may also be a medium size heteroalkyl having 1 to 9 carbon atoms. The heteroalkyl group could also be a lower heteroalkyl having 1 to 4 carbon atoms. The heteroalkyl group may be designated as "$C_{1-4}$ heteroalkyl" or similar designations. The heteroalkyl group may contain one or more heteroatoms. By way of example only, "$C_{1-4}$ heteroalkyl" indicates that there are one to four carbon atoms in the heteroalkyl chain and additionally one or more heteroatoms in the backbone of the chain. Unless indicated to the contrary, the term "heteroalkyl" refers to a group that is not further substituted.

As used herein, "carbocyclyl" means a non-aromatic cyclic ring or ring system containing only carbon atoms in the ring system backbone. When the carbocyclyl is a ring system, two or more rings may be joined together in a fused, bridged or spiro-connected fashion. Carbocyclyls may have any degree of saturation provided that at least one ring in a ring system is not aromatic. Thus, carbocyclyls include cycloalkyls, cycloalkenyls, and cycloalkynyls. In some embodiments, the carbocyclyl group has from 3 to 20 carbon atoms, although the present definition also covers the occurrence of the term "carbocyclyl" where no numerical range is designated. The carbocyclyl group may also be a medium size carbocyclyl having 3 to 10 carbon atoms. The carbocyclyl group could also be a carbocyclyl having 3 to 6 carbon atoms. The carbocyclyl group may be designated as "$C_{3-6}$ carbocyclyl" or similar designations. Examples of carbocyclyl rings include, but are not limited to, cyclopropyl, cyclobutyl, cyclopentyl, cyclohexyl, cyclohexenyl, 2,3-dihydro-indene, bicycle[2.2.2]octanyl, adamantyl, and spiro[4.4]nonanyl. Unless indicated to the contrary, the term "carbocyclyl" refers to a group that is not further substituted As used herein, "cycloalkyl" means a fully saturated carbocyclyl ring or ring system, according to any of the embodiments set forth above for carbocyclyl. Examples include cyclopropyl, cyclobutyl, cyclopentyl, cyclohexyl, and adamantyl.

Chemical structures are often shown using the "skeletal" format, such that carbon atoms are not explicitly shown, and hydrogen atoms attached to carbon atoms are omitted entirely. For example, the structure

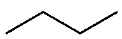

represents putane (i.e., n-putane). Furthermore, aromatic groups, such as benzene, are represented by showing one of the contributing resonance structures. For example, the structure

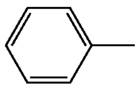

represents toluene.

Other terms are defined in other portions of this description, even though not included in this subsection.

Aminoquinoline Compounds

The disclosure provides methods to synthesize certain aminoquinoline compounds, particularly compounds of formula (Ia):

(Ia)

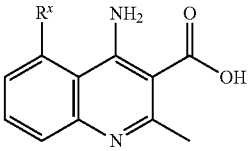

or comestibly acceptable salts thereof, wherein: $R^x$ is —F or —O—$R^1$; and $R^1$ is a $C_{1-20}$ hydrocarbyl moiety, where one or more carbon atoms in the hydrocarbyl moiety are optionally replaced by a heteroatom selected from the group consisting of oxygen, nitrogen, and sulfur.

In some embodiments, $R^x$ is —F. In some embodiments, $R^x$ is —O—$R^1$.

$R^1$ can have any suitable value according to the definition set forth above. In some embodiments, $R^1$ is a $C_{1-15}$ hydrocarbyl moiety, where one or more carbon atoms in the hydrocarbyl moiety are optionally replaced by a heteroatom selected from the group consisting of oxygen, nitrogen, and sulfur. In some embodiments, $R^1$ is a $C_{1-12}$ hydrocarbyl moiety, where one or more carbon atoms in the hydrocarbyl moiety are optionally replaced by a heteroatom selected from the group consisting of oxygen, nitrogen, and sulfur. In some embodiments, $R^1$ is a $C_{1-6}$ alkyl group, such as methyl, ethyl, propyl, isopropyl, butyl, isobutyl, sec-butyl, tert-butyl, pentyl, hexyl, and the like. In some other embodiments, $R^1$ is a $C_{3-10}$ cycloalkyl group, such as cyclopentyl, cyclohexyl, and the like. In some embodiments, $R^1$ is a $C_{1-10}$ heteroalkyl group. For example, in some such embodiments, $R^1$ is —($C_{1-6}$ alkylene)-C(O)—NH—($C_{1-6}$ alkyl). In some further such embodiments, $R^1$ is —$CH_2$—$C(CH_3)_2$—C(O)—NH—($C_{1-6}$ alkyl).

The term "alkylene" is understood as alkanediyl; i.e. an alkane group with two free valencies such as —$(CH_2)_4$—.

The skilled artisan will recognize that some structures described herein may be resonance forms or tautomers of compounds that may be fairly represented by other chemical structures, even when kinetically; the artisan recognizes that such structures may only represent a very small portion of a sample of such compound(s). Such compounds are considered within the scope of the structures depicted, though such resonance forms or tautomers are not represented herein.

Isotopes may be present in the compounds described. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

In some embodiments, the compounds disclosed herein are capable of forming acid and/or base salts by virtue of the presence of amino and/or carboxyl groups or groups similar thereto. Comestibly acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Physiologically acceptable salts can be formed using inorganic and organic bases. Inorganic bases from which salts can be derived include, for example, bases that contain sodium, potassium, lithium, ammonium, calcium, magnesium, iron, zinc, copper, manganese, aluminum, and the like; particularly preferred are the ammonium, potassium, sodium, calcium and magnesium salts. In some embodiments, treatment of the compounds disclosed herein with an inorganic base results in loss of a labile hydrogen from the compound to afford the salt form including an inorganic cation such as $Li^+$, $Na^+$, $K^+$, $Mg^{2+}$ and $Ca^{2+}$ and the like. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine.

In some embodiments, the aminoquinoline compound is an acid addition salt of a compound of formula (I) according to any of the embodiments set forth above. In some further such embodiments, the acid addition salt is a hydrochloride salt, a sulfate salt, or a phosphate salt.

Methods of Synthesis

One step of the synthetic methods disclosed herein involves reacting a compound of formula (Ib)

(Ib)

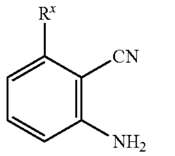

with a compound of formula (Ic)

(Ic)

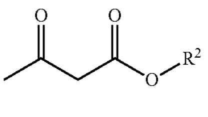

to form a compound of formula (Id)

(Id)

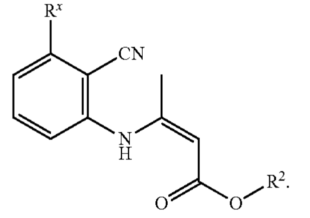

For the aminobenzonitrile compound of formula (Id), $R^2$ can have any suitable value consistent with the definition set forth above. In some embodiments, $R^2$ is methyl, ethyl, isopropyl, propyl, butyl, or tert-butyl. In some embodiments, $R^2$ is methyl. In some embodiments, $R^2$ is ethyl. The aminobenzonitrile compound of formula (Ib) can be generated in any suitable means. For example, in some embodiments where $R^x$ is —O—$R^1$, the compound of formula (Ib) is formed by reacting 2-amino-6-fluorobenzonitrile with a compound of formula $R^1$—OH to form the compound of formula (Ib). Said reaction step to obtain the compound of formula (Ib) where $R^x$ is —O—$R^1$ can be carried out under suitable conditions and in the presence of suitable solvents. In some embodiments, the reaction is carried out in the presence of an organic base, such as metal alkoxide wherein the metal is an alkali metal. Examples include, without limitation, potassium tert butoxide and potassium methoxide. In some embodiments, no additional solvent is present. But, in some embodiments, one or more additional solvents can be added. Suitable solvents include organic solvents, such as toluene, xylenes, alkanes (such as hexanes), ether (such as tetrahydrofuran or 2-methyltetrahydrofurane) and organic alcohols (such as ethanol).

The enamine formation reaction step described above (step (a)) can be carried out under suitable conditions and in the presence of suitable solvents. In some embodiments, the reaction is carried out in the presence of an organic acid, such as a hydrocarbyl sulfonic acid. Examples include, without limitation, methanesulfonic acid and p-tolylsulfonic acid. In some embodiments, no additional solvent is present, as, in many instances, the acetoacetate reactant is liquid at relevant reaction temperatures. But, in some embodiments, one or more additional solvents can be added. Suitable solvents include organic solvents, such as toluene, xylenes, alkanes (such as hexanes), and organic alcohols (such as ethanol). In some cases, an alkyl acetoacetate (such as ethyl acetoacetate) can be added in excess and serve as both a reactant and a solvent.

The enamine formation reaction generates water as a reaction byproduct. In some embodiments, the method comprises removing at least a portion of the water generated by the reaction is removed. For example, in some embodiments, at least 20%, or at least 30%, or at least 40%, or at least 50%, or at least 60%, or at least 70%, or at least 80%, or at least 90%, of the water generated by the reaction is removed from the reaction vessel, for example, by distillation. In some such embodiments, additional acetoacetate (compound of formula (Ic)) is added to the reaction vessel.

The reaction can be carried out at any suitable temperature and pressure. In embodiments where at least a portion of the water byproduct is removed during the reaction, it may be desirable for the temperature to be sufficiently high to allow the water to be removed as water vapor. Thus, in some embodiments, the reaction is carried out at a temperature ranging from 50 °C to 100 °C, or from 60 °C to 90 °C, or from 70 °C to 80 °C. In some embodiments, the enamine formation reaction is carried out at atmospheric pressure or at reduced pressure relative to ambient atmospheric pressure. For example, in some embodiments, the reaction is carried out at an absolute pressure ranging from 1 mbar to 500 mbar, or from 1 mbar to 200 mbar, or from 1 mbar to 100 mbar, or from 1 mbar to 50 mbar, or from 5 mbar to 50 mbar, or from 5 mbar to 40 mbar.

The methods disclosed herein comprise reacting the enamine compound of formula (Id), generated according to any of the embodiments set forth above, to form the aminoquinoline compound of formula (Ia). In some embodiments, the reaction is two or more sub-steps, which, in some embodiments, can be carried out in the same reaction vessel. In some embodiments, the enamine compound is reacted with an alkali metal alkoxide (such as sodium ethoxide). The reaction can be carried out in any suitable solvent. For example, in some embodiments, the solvent is a polar organic solvent such as an aliphatic alcohol, such as ethanol. The addition of the alkali metal oxide induces cyclization to form a 4-aminoquinoline compound having an alkyl ester substituent at the 3-position. In a second substep, the alkyl ester group is converted to a free carboxylic acid. This can be carried out by any suitable means. In some embodiments, the resulting ester-substituted compound is saponified using a base, such as aqueous sodium hydroxide, followed by acidification using a suitable acid, such as hydrochloric acid, sulfuric acid, phosphoric acid, acetic acid, and the like. In general, the acidification is carried out to bring the reaction medium to a pH ranging from 6 to 8, namely, about 7. The resulting compound is an aminoquinoline compound of formula (Ia).

In some embodiments where RY is —F, it may be desirable to replace the fluorine radical of the aminoquinoline compound of formula (Ia) with —O—$R^1$. This can be carried out by any suitable means, such as the one reported above.

In some embodiments, it may be desirable to form salts, such as acid addition salts, of the aminoquinoline compound of formula (Ia). This can be done to enhance water solubility to allow for the inclusion of such compounds in salt form in comestible products, such as those described in PCT Publication No. WO 2013/025560. Such salts can be formed by any suitable means. In some embodiments, the aminoquinoline compound of formula (I) is reacted with an acid, such as sulfuric acid or phosphoric acid, in an aqueous solvent system. The solvent system comprises water, and, optionally, one or more additional water-miscible solvents. In some embodiments, the aqueous solvent system is substantially free of organic alcohols, e.g., the aqueous solvent system comprises no more than 5%, or no more than 4%, or no more than 3%, or no more than 2%, or no more than 1%, of organic alcohols, based on the total weight of the aqueous solvent system. In some embodiments, the aqueous solvent system comprises water and acetone, for example, in relative weight ratios ranging from 1:2 to 10:1. Thereafter, a water immiscible (20% or less soluble in water at 25 °C) solvent system is added to the mixture, for example, in much greater relative amounts, to induce crystallization of the salt of the aminoquinoline compound in an organic phase. In some embodiments, the water-immiscible solvent is ethyl acetate.

In some embodiments, the salt formation is carried out in the same pot as the previous step, where the salt formation represents a continuation of the acidification following saponification. In such cases, the same acid can be used for the acidification and the salt formation, and the acid is added until the pH becomes much lower, for example, in the range of 1 to 4, namely, about 2.

EXAMPLES

To further illustrate this invention, the following examples are included, wherein the abbreviations have the usual meaning in the art, the temperatures are indicated in degrees centigrade (°C). NMR spectra were acquired using either a Bruker Avance II Ultrashield 400 plus operating at 400 MHZ, ($^1$H) and 100 MHz ($^{13}$C) or a Bruker Avance III 500 operating at 500 MHZ ($^1$H) and 125 MHz ($^{13}$C) or a Bruker Avance III 600 cryoprobe operating at 600 MHz ($^1$H) and 150 MHz ($^{13}$C). Spectra were internally referenced relative to tetramethyl silane 0.0 ppm. $^1$H NMR signal shifts are expressed in δ ppm, coupling constants (J) are expressed in Hz with the following multiplicities: s, singlet; d, doublet; t, triplet; q, quartet; m, multiplet; b, broad (indicating unresolved couplings) and were interpreted using Bruker Topspin software. $^{13}$C NMR data are expressed in chemical shift δ ppm and hybridization from DEPT 90 and DEPT 135 experiments, C, quaternary; CH, methine; $CH_2$, methylene; $CH_3$, methyl. The examples should not, of course, be construed as specifically limiting the invention. Variations of these examples within the scope of the claims are within the purview of one skilled in the art and are considered to fall within the scope of the invention as described, and claimed herein. The reader will recognize that the skilled artisan, armed with the present disclosure, and skill in the art is able to prepare and use the invention without exhaustive examples.

Example 1—Aminoquinoline Synthesis

Toluene (577 mL, 5418 mmol, 2.56 eq.) was poured in a 1.7 L autoclave 3-hydroxy-2,2-dimethylpropanoic acid (250 g, 2116 mmol) was then added to the solution while stirring. The suspension was heated up to 80 °C. Isopropylamine (184 mL, 2137 mmol, 1.01 eq.) was added in 4 h. The mixture was cooled to 25 °C and the rest of isopropylamine (273 mL, 3174 mmol, 1.5 eq.) and boric acid (5.23 g, 85 mmol) were added in the reactor. The mixture was heated up to 175 °C (internal temperature, internal pressure 13 bar) for 24 h. The mixture was cooled to 25 °C and removed (1047.92 g) from the reactor. Isopropylamine and toluene were distilled (80 °C, 500-3 mbar) from the reaction mixture (350.77 g). Sodium carbonate (9.6 g) and polyethylene glycol 400 (101.1 g) were added and the mixture was distilled under a pressure of 1 mbar at a vapor temperature of 117-118 °C to obtain 3-hydroxy-N-isopropyl-2,2-dimethylpropanamide with a molar yield of 91% and a purity of 98.8%. Identity of the compound was confirmed by GC-MS, $^1$H NMR, and $^{13}$C NMR.

2-Methyltetrahydrofuran (MeTHF) (584 mL, 5805 mmol) and potassium tert-butoxide (180 g, 1556 mmol) were charged in a 1.5 L double jacketed reactor. The suspension was heated up to 60 °C. A solution of 3-hydroxy-N-isopropyl-2,2-dimethylpropanamide (249 g, 1564 mmol) in methyltetrahydrofuran (249.0 g) was added in 1 hr. The mixture was heated up to 70 °C (set point pot). A solution of 2-amino-6-fluorobenzonitrile (199 g, 1462 mmol) in methyltetrahydrofuran (700 g) was added in 2 h. The brown mixture was stirred at 70 °C during 3 hrs after the end of the introduction. Part of the solvent (1421.54 g, 92% MeTHF, 8% t-BuOH) was distilled under reduced pressure (Tmax=82 °C, p=800-600 mbar). The mixture was maintained at 82 °C and PhMe (700.0 g) and 15% aqueous acetic acid (169.6 g) were added. The aqueous phase (221.4 g, pH=7-8) was separated and discarded. The organic phase was washed three times with 100.0 g water. The mixture was dried distilling the water azeotropically (Tpot.max=111 °C, Tvapour.max=106 °C, 268.42 g of PhMe and 51.2 g aqueous phase recovered). The mixture was cooled to 90 °C and seeded with solid 3-(3-amino-2-cyanophenoxy)-N-isopropyl-2,2-dimethylpropanamide (1.0 g). The mixture was cooled to −15 °C. The slurry was filtered and the cake was washed with cold (5 °C) methyl tert-butyl ether (twice 100.0 g). After drying (25 °C, 0.5 mbar), 3-(3-amino-2-cyanophenoxy)-N-isopropyl-2,2-dimethylpropanamide (335.07 g, 1217 mmol, 83% yield) was obtained as beige crystals. Its identity was confirmed by GC-MS, $^1$H NMR, and $^{13}$C NMR.

Methyl 3-oxobutanoate (980 mL, 9079 mmol) and 3-(3-amino-2-cyanophenoxy)-N-isopropyl-2,2-dimethylpropanamide (250 g, 908 mmol) were charged in a 1.5 L double-jacketed reactor. 4-Methylbenzenesulfonic acid hydrate (1.727 g, 9.08 mmol) was added under nitrogen at room temperature. The suspension was heated up to 75 °C. Methyl 3-oxobutanoate was distilled (650 g, 20 mbar) over 8 hours while the volume of the solution was kept constant by adding fresh methyl 3-oxobutanoate (794 g). The mixture was cooled to 65 °C and seeded with solid (Z)-methyl 3-(2-cyano-3-(3-(isopropylamino)-2,2-dimethyl-3-oxopropoxy)phenylamino) but-2-enoate (1.0 g). The mixture was cooled to 10 °C and quenched by addition of aqueous $NaHCO_3$ (9.64 ml, 9.99 mmol). The slurry was filtered and the cake was washed with ethyl acetate (100 mL×2). After drying on the rotatory evaporator (80 °C, 500-3 mbar), (Z)-methyl-3-(2-cyano-3-(3-(isopropylamino)-2,2-dimethyl-3-oxopropoxy)phenylamino) but-2-enoate (246.19 g, 659 mmol, 73% yield) was obtained as a white solid. Its identity was confirmed by $^1$H NMR and $^{13}$C NMR.

1H NMR (400 MHZ, CDCl3) δ 10.66 (s, 1H), 7.41 (t, J=8.3 Hz, 1H), 6.78 (d, J=0.7 Hz, 1H), 6.70 (d, J=0.8 Hz, 1H), 5.95 (d, J=8.0 Hz, 1H), 4.87 (d, J=0.8 Hz, 1H), 4.13-4.04 (m, 1H), 4.02 (s, 2H), 2.06 (d, J=0.7 Hz, 3H), 1.34 (s, 7H), 1.18 (d, J=6.6 Hz, 7H).

13C NMR (101 MHz, $CDCl_3$) δ 174.20, 170.16, 161.27, 156.44, 143.81, 133.97, 116.43, 114.12, 107.45, 97.22, 90.20, 75.64, 50.70, 42.71, 41.70, 22.59, 20.32.

(Z)-Methyl-3-(2-cyano-3-(3-(isopropylamino)-2,2-dimethyl-3-oxopropoxy)-phenylamino) but-2-enoate (183.1 g, 490 mmol) was stirred in absolute ethanol (725 mL) at RT under nitrogen in a 1.5 L double-jacketed reactor. Sodium ethylate 21% in solution in ethanol (208 ml, 556 mmol) was added under nitrogen. The reaction mixture was stirred for 4.5 h at 80 °C. Water (729 mL) and NaOH solution 30% (108 ml, 1079 mmol) was added to the mixture and stirred for 8 h at 100 °C. Part of the solvent (893.68 g, 78.3% EtOH, 21.7% H2O) was distilled (Tmax=110 °C). The mixture was cooled to 90 °C and sulfuric acid 50% in water (150.49 g, 809 mmol) was added to the solution until pH-6.8. The white precipitation was filtered off at 40 °C and the cake was washed with EtOAc (100 ml×2) to give the title compound (167.07 g, 465 mmol, 95% yield). Its identity was confirmed by LC-MS, $^1$H NMR, and $^{13}$C NMR.

Example 2—Synthesis of Sulfate Salt of Aminoquinoline

4-Amino-5-(3-(isopropylamino)-2,2-dimethyl-3-oxopropoxy)-2-methylquinoline-3-carboxylic acid (100.04 g, 278 mmol), $H_2O$ (50.0 ml, 2776 mmol), acetone (51.1 ml, 696 mmol) and sulfuric acid 50% in water (18.98 ml, 178 mmol) were added to a 1 L flask at RT. The mixture was heated at 78 °C for 30 min. Ethyl acetate (146 ml, 1489 mmol) was added dropwise over 30 min into the limpid solution. The mixture was cooled to 25 °C and seeded with solid 4-amino-5-(3-(isopropylamino)-2,2-dimethyl-3-oxo-propoxy)-2-methylquinoline-3-carboxylic acid. A mixture of acetone (51.1 ml, 696 mmol) and ethyl acetate (146 ml, 1489 mmol) was then added to the solution. The slurry was filtered and the cake was washed with ethyl acetate (100 mL×3). After drying (80 °C, 500-3 mbar), 3-carboxy-5-(3-(isopropylamino)-2,2-dimethyl-3-oxopropoxy)-2-methylquinolin-4-ammonium sulfate (102.12 g, 125 mmol, 90% yield) was obtained as white crystals. Its identity was confirmed by LC-MS, $^1H$ NMR, and $^{13}C$ NMR.

The invention claimed is:

1. A method of making a compound of formula (Ia)

(Ia)

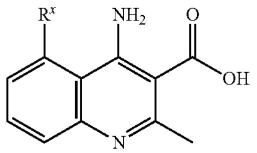

or a comestibly acceptable salt thereof, the method comprising:

(a) reacting a compound of formula (Ib)

(Ib)

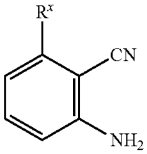

with a compound of formula (Ic)

(Ic)

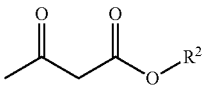

to form a compound of formula (Id)

(Id)

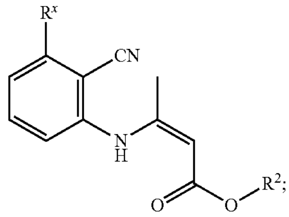

and (b) reacting the compound of formula (Id) of (a) to form a compound of formula (Ia); wherein:

$R^x$ is —F or —O—$R^1$;

$R^1$ is $C_{1-20}$ hydrocarbyl, wherein one or more of the carbon atoms of the hydrocarbyl group are replaced by nitrogen, oxygen, or sulfur; and $R^2$ is $C_{1-6}$ alkyl.

2. The method of claim 1, wherein the reacting step (b) comprises cyclizing the enamine compound of formula (Id) followed by saponification and acidification to form the compound of formula (Ia).

3. The method of claim 1, wherein $R^x$ is —O—$R^1$.

4. The method of claim 1, wherein $R^x$ is —F.

5. The method of claim 1, wherein $R^x$ is —O—$R^1$, and the compound of formula (Ib) is formed by reacting 2-amino-6-fluorobenzonitrile with a compound of formula $R^1$—OH to form the compound of formula (Ib).

6. The method of claim 1, wherein the method is a method of making an acid addition salt of the compound of formula (Ia), and comprises (c) reacting the compound of formula (Ia) of (b) with an acid to form an acid addition salt of the compound of formula (Ia).

7. The method of claim 6, wherein the acid is sulfuric acid, and the acid addition salt of the compound of formula (Ia) is a sulfate salt of the compound of formula (Ia).

8. The method of claim 6, wherein the acid is phosphoric acid, and the acid addition salt of the compound of formula (Ia) is a phosphate salt of the compound of formula (Ia).

9. The method of claim 1, wherein $R^2$ is methyl, ethyl, propyl, isopropyl, butyl, or tert-butyl.

10. The method of claim 1, wherein $R^1$ is $C_{1-6}$ alkyl, $C_{3-10}$ cycloalkyl, or $C_{1-10}$ heteroalkyl.

11. The method of claim 1, wherein $R^1$ is $C_{1-6}$ alkyl or $C_{3-10}$ cycloalkyl, such as methyl, ethyl, propyl, isopropyl, isobutyl, cyclopentyl, or cyclohexyl.

12. The method of claim 1, wherein $R^1$ is —($C_{1-6}$ alkylene)-C(O)—NH—$C_{1-6}$ alkyl.

* * * * *